United States Patent
Raimondo et al.

(10) Patent No.: US 11,559,244 B2
(45) Date of Patent: Jan. 24, 2023

(54) SYSTEM AND METHODS FOR CONSCIOUSNESS EVALUATION IN NON-COMMUNICATING SUBJECTS

(71) Applicants: ICM—INSTITUT DU CERVEAU ET DE LA MOELLE ÉPINIÈRE, Paris (FR); INSERM, Paris (FR); CNRS, Paris (FR); APHP, Paris (FR); Sorbonne-Université, Paris (FR)

(72) Inventors: Federico Raimondo, Beaufays (BE); Jacobo D Sitt, Paris (FR); Lionel Naccache, Paris (FR); Diego Fernandez Slezak, Buenos Aires (AR)

(73) Assignees: ICM—INSTITUT DU CERVEAU ET DE LA MOELLE ÉPINIÈRE, Paris (FR); INSERM (INSTITUT NATIONAL DE LA SANTÉ ET DE LA RECHERCHE MÉDICALE), Paris (FR); CNRS (CENTRE NATIONAL DE LA RECHERCHE SCIENTIFIQUE), Paris (FR); APHP, Paris (FR); SORBONNE UNIVERSITÉ, Paris (FR)

( * ) Notice: Subject to any disclaimer, the term of this patent is extended or adjusted under 35 U.S.C. 154(b) by 1051 days.

(21) Appl. No.: 16/127,816

(22) Filed: Sep. 11, 2018

(65) Prior Publication Data
US 2020/0077918 A1  Mar. 12, 2020

(51) Int. Cl.
*A61B 5/00* (2006.01)
*A61B 5/352* (2021.01)
(Continued)

(52) U.S. Cl.
CPC .............. *A61B 5/38* (2021.01); *A61B 5/0048* (2013.01); *A61B 5/0205* (2013.01);
(Continued)

(58) Field of Classification Search
None
See application file for complete search history.

(56) References Cited

U.S. PATENT DOCUMENTS

| | | | |
|---|---|---|---|
| 2013/0109995 A1* | 5/2013 | Rothman | A61B 5/369 600/544 |
| 2013/0184603 A1* | 7/2013 | Rothman | A61B 5/369 600/544 |
| 2013/0245422 A1* | 9/2013 | D'arcy | A61B 5/316 600/409 |

FOREIGN PATENT DOCUMENTS

EP  2 682 053 A1  1/2014

OTHER PUBLICATIONS

Raimondo et al. Probing consciousness in heart-brain interactions in severely brain-injured patients. 2016. (Year: 2016).*
(Continued)

*Primary Examiner* — Etsub D Berhanu
(74) *Attorney, Agent, or Firm* — Nixon & Vanderhye

(57) ABSTRACT

Disclosed is a method for the generation of a consciousness indicator for a non-communicating subject, including the steps of generating an auditory stimulation, receiving an electrocardiographic signal of the subject obtained from a recording during the generation of the auditory stimulation, extracting at least one feature from the electrocardiographic signal and deducing a consciousness indicator from an analysis of the electrocardiographic feature.

9 Claims, 4 Drawing Sheets

(51) Int. Cl.
    A61B 5/38      (2021.01)
    A61B 5/024     (2006.01)
    A61B 5/0205    (2006.01)
    A61B 5/316     (2021.01)
    A61B 5/349     (2021.01)

(52) U.S. Cl.
    CPC .......... *A61B 5/02405* (2013.01); *A61B 5/316* (2021.01); *A61B 5/349* (2021.01); *A61B 5/352* (2021.01); *A61B 5/7264* (2013.01)

(56) References Cited

OTHER PUBLICATIONS

Gutierrez et al. Heart rate variability changes induced by auditory stimulation in persistent vegetative state. International Journal on Disability and Human Development, Dec. 2010. (Year: 2010).*

Faugeras et al. Event related potentials elicited by violations of auditory regularities in patients with impaired consciousness. Neuropsychologia 50 (2012) 403-418. (Year: 2012).*

Karoui et al. Event-Related Potential, Time-frequency, and Functional Connectivity Facets of Local and Global Auditory Novelty Processing: An Intracranial Study in Humans. Cerebral Cortex—Jun. 2014. (Year: 2014).*

Ray et al. Morphological Variations in ECG During Music-Induced Change in Consciousness. Oct. 30-Nov. 2, 1997. (Year: 1997).*

Riganello et al. Heart rate variability: An index of brain processing in vegetative state? An artificial intelligence, data mining study. Clinical Neurophysiology 121 (2010) 2024-2034. (Year: 2010).*

Bekinschtein et al. Neural signature of the conscious processing of auditory regularities. PNAS. Feb. 3, 2009. (Year: 2009).*

Raimondo et al., "Brain-Heart Interactions Reveal Consciousness in Noncommunicating Patients," American Neurological Association, Annals of Neurology, vol. 82, No. 4, Oct. 1, 2017, pp. 578-591.

Elgendi, "Fast QRS Detection with an Optimized Knowledge-Based Method: Evaluation on 11 Standard ECG Databases," PLoS One, vol. 8, No. 9, Sep. 2013, e73557, 18 pages.

* cited by examiner

SYSTEM AND METHODS FOR CONSCIOUSNESS EVALUATION IN NON-COMMUNICATING SUBJECTS

FIELD OF INVENTION

The present invention pertains to the field of physiological signal evaluation. In particular, the invention relates to the reception and processing of at least one physiological signal in order to evaluate the state of consciousness of non-communicating subjects.

BACKGROUND OF INVENTION

Patients with disorders of consciousness (DOC) are characterized by preserved wakefulness in the absence of clear evidence of awareness such that they remain unable to communicate with their surroundings.

For example, patients in a vegetative state/unresponsive wakefulness syndrome (VS/UWS) open their eyes, but they do not show conscious responses to sensory stimulation. When patients exhibit signs of fluctuating yet reproducible remnants of nonreflex behavior, such as visual pursuit, they are considered to be in a minimally conscious state (MCS). The diagnostic assessment of patients with disorders of consciousness is mainly based on the observation of motor and oculomotor behaviors at the bedside. The evaluation of nonreflex behavior, however, is not straightforward, as patients can fluctuate in terms of vigilance, and may suffer from cognitive and/or sensory impairments, from small or easily exhausted motor activity and pain, which may lead in the underestimation of the level of consciousness. Previous work employing data-driven analyses with neuroimaging and neurophysiological tools suggest relatively accurate patient diagnosis and prediction of clinical outcome. Most of this works uses measurements of brain electrophysiological activity by means of functional MRI or high density electroencephalograms (EEG).

However, neuroimaging, such as functional MRI and neurophysiological techniques are generally complex to implement, especially on patients that are in a vegetative state/unresponsive wakefulness syndrome or minimally conscious state. To perform neuroimaging, the patient usually needs to be moved from his bed to an imaging facility. When using neurophysiological techniques, the neurophysiological signal may be acquired on site without need to move the patient. However, due to level of accuracy needed to this task, the neurophysiological signal has to be acquired with high spatial density (i.e. high density EEG), producing a large amount of raw data which requires important calculation power. Therefore, data cannot be analyzed on site but need to be transferred for calculation to a remote device or server. Furthermore, neurophysiological techniques are sensible to electric signal of the order of the hundreds of $\mu V$ in order to detect brain electric signal on the scalp of the subject and therefore are sensible as well to the electromagnetic noise.

In this context, the invention herein described proposes a solution allowing accurate patient diagnosis and prediction of clinical outcome, using physiological techniques that are noise robust.

SUMMARY OF THE INVENTION

The present invention relates to a method for the generation of a consciousness indicator for anon-communicating subject, comprising:

generating an auditory stimulation, said auditory stimulation comprising multiple auditory trials having a predefined intertrial interval, each auditory trial formed by N consecutive auditory stimuli having a predefined time duration with a predefined gap between the auditory stimuli onsets, wherein the auditory stimulation comprises a first percentage of local standard trials comprising N identical auditory stimuli and a second percentage of locally deviant trials comprising the first N-1 identical auditory stimuli and the Nth auditory stimulus different from the preceding N-1 auditory stimuli, wherein N is equal or superior to 2;

receiving an electrocardiographic signal of the subject obtained from a recording during the generation of the auditory stimulation;

extracting at least one feature from the electrocardiographic signal;

deducing a consciousness indicator from an analysis of the electrocardiographic feature.

The method for the consciousness evaluation of non-communicating subjects of the present invention is configured to use electrocardiographic signal. Indeed, cardiac activity is a peripheral body signal that is linked to cognitive process and the analysis of the modulation of the cardiac cycle during an auditory protocol provides advantageous information on residual cognitive processing in the subject allowing an accurate assessment of patient with disorders of consciousness.

According to one embodiment, the extraction step and the deduction step comprise:

performing a delineation of the EKG electrocardiographic signal identifying for each heart beat a QRS complex;

calculating the heart rate and heart rate variability for the electrocardiographic signal from the delineation of the electrocardiographic signal;

defining for each trial a time interval as the interval between the onset of the Nth auditory stimulus and the following R peak and calculating the consciousness indicator as a phase shift in the cardiac cycle in the time interval.

The phase shift in the cardiac cycle is an advantageous marker to characterize the consciousness state of subject having disorders of consciousness. Furthermore, the phase shift in the cardiac cycle in the time interval locked to the auditory stimulation is an easy parameter to extract from the electrocardiographic signal.

According to one embodiment, the method further comprises a step of receiving an electroencephalographic signal of the subject recorded during the generation of the auditory stimulation.

According to one embodiment, the received electrocardiographic signal is extracted from the electroencephalographic signal.

According to one embodiment, the extraction step and the deduction step comprise:

extracting at least one EKG feature from the electrocardiographic signal associated to cognitive processes; and generating a consciousness indicator by using the EKG features as input of a classifier.

According to one embodiment, the method further comprises the steps of:

measuring an electroencephalographic signal of the subject during the generation of the auditory stimulation;

extracting at least one EEG feature from the electroencephalographic signal; and using the EEG feature(s) as further input of the classifier to generate a consciousness indicator.

According to one embodiment, the classifier is a previously trained machine learning technique.

According to one embodiment, the method further comprises a step of comparison of the consciousness indicator to a predefined threshold.

The present invention further relates to a program comprising instructions which, when the program is executed by a computer, cause the computer to carry out the steps of the method according to any one of the embodiments described hereabove.

The present invention also relates to a non-transitory computer readable medium comprising instructions which, when the program is executed by a computer, cause the computer to carry out the steps of the method according to any one of the embodiments described hereabove.

Yet another aspect of the present invention relates to a system for the generation of a consciousness indicator for a non-communicating subject, comprising:
- a stimuli generator configured to generate an auditory stimulation, said auditory stimulation comprising multiple stimulation trials having a predefined intertrial interval, each stimulation trial formed by N consecutive auditory stimuli having a predefined time duration with a predefined gap between the auditory stimuli onsets, wherein the auditory stimulation comprises a first percentage of local standard trials comprising N identical auditory stimuli and a second percentage of locally deviant trials comprising the first N−1 identical auditory stimuli and the Nth auditory stimulus different from the preceding N−1 auditory stimuli;
- an extraction module configured to obtain an electrocardiographic signal of the subject during the generation of the auditory stimulation; and
- a calculation module configured to extract at least one feature from the electrocardiographic signal and deduce a consciousness indicator from an analysis of the electrocardiographic feature.

Definitions

In the present invention, the following terms have the following meanings:

"Electrode" refers to a conductor used to establish electrical contact with a nonmetallic part of a circuit, preferably a subject body. For instance, EEG electrodes are small metal discs usually made of stainless steel, tin, gold, silver covered with a silver chloride coating; there are placed on the scalp at specific positions.

"Electrocardiographic signal" refers to the signal recording the electrical conduction in the heart. Said cardiac signal may be for instance an electrocardiogram (EKG or ECG) or an endocardiogram. Such signals may have one or more channels, called leads. It may be short term (10 seconds in standard EKGs) or long term (several days in Holters).

"Electroencephalogram" or "EEG" refers to the tracing of brain waves, by recording the electrical activity of the brain from the scalp, made by an electroencephalograph.

"Electroencephalograph" refers to an apparatus for amplifying and recording brain waves.

"Heart rate variability (HRV)" refers to the physiological phenomenon of variation in the time interval between heartbeats. It is measured by the variation in the beat-to-beat interval.

"Mismatch negativity (MMN)" refers to a brain response to violations of a rule, established by a sequence of sensory stimuli (typically in the auditory domain). The mismatch negativity reflects the brain's ability to perform automatic comparisons between consecutive stimuli and provides an electrophysiological index of sensory learning and perceptual accuracy.

"P300 wave" refers to event related potential (ERP) component elicited in the process of decision making. More specifically, the P300 is thought to reflect processes involved in stimulus evaluation or categorization.

"Subject" refers to a mammal, preferably a human. In the sense of the present invention, a subject may be a patient, i.e. a person receiving medical attention, undergoing or having underwent a medical treatment, or monitored for the development of a disease.

BRIEF DESCRIPTION OF THE DRAWINGS

Features and advantages of the invention will become apparent from the following description of embodiments of a method and a system for the generation of a consciousness indicator for non-communicating subjects according to the invention, this description being given merely by way of example and with reference to the appended drawings in which.

DETAILED DESCRIPTION

This invention relates to a method for characterizing the consciousness state of subjects with disorders of consciousness. To this end, the method is configured to receive and analyze at least cardiac activity data comprising information linked to cognitive process in the subject so to generate a consciousness indicator. Indeed, cardiac activity is a peripheral body signal that is linked to cognitive processes.

Figure 1:
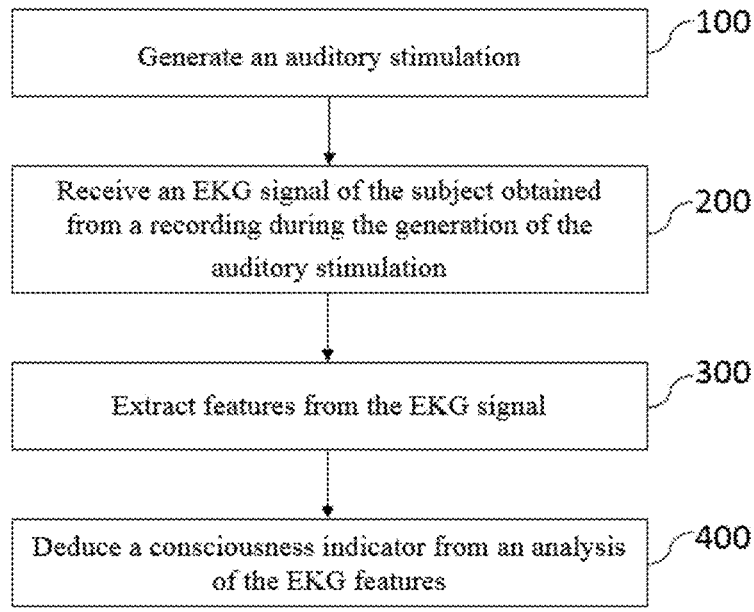
FIG. 1 is a flowchart showing the main steps of the method according to the present invention.

As shown in FIG. 1, the method of the present invention comprises four main steps, starting from the generation of an auditory stimulation 100. The second main step 200 consists in the reception of an electrocardiographic signal recorded from the subject during the auditory stimulation. The third step 300 extracts the features from the electrocardiographic signal while the last step 400 is configured to deduce a consciousness indicator from an analysis of the EKG features.

The auditory stimulation 100 is configured to induce a cognitive process in the stimulated subject. The human brain has the ability to extract patterns or regularities in its environment, e.g. object A is always followed by object B but never by object C. The brain can detect transitional probabilities in an automatic way, i.e. even when the subject's attention is distracted, or when stimuli are presented below the threshold of awareness. Automatic brain responses to a violation of a rule (or regularity) can also be detected if the stimuli are in close or local temporal vicinity (i.e. within few seconds). Mismatch responses can be produced with complex sequences such as a melody or a rhythm even in unconscious subjects.

According to one embodiment, the auditory stimulation comprises multiple auditory trials having a predefined intertrial interval, each auditory trial formed by N consecutive auditory stimuli having a predefined time duration with a predefined gap between the auditory stimuli onsets. In this embodiment, the auditory stimulation has a first percentage of local standard trials comprising N identical auditory stimuli and a second percentage of locally deviant trials comprising the first N−1 identical auditory stimuli and the $N^{th}$ auditory stimulus different from the preceding N−1 auditory stimuli, wherein N is equal or superior to 2

In one preferred embodiment, the cognitive processing is prompted by means of auditory 'local-global' paradigm. This 'local-global' paradigm is based on an auditory oddball paradigm in which a sequence of sounds is presented at each auditory trial. The sequence is composed of a standard sound repeated a certain number of times, followed by a deviant sound. The comparison to a condition in which all the sounds of the sequence are standard typically reveals the occurrence of the mismatch negativity. Crucially, if the deviant sequence is highly frequent within a block, the subjects would expect the last sound to be deviant. The sequence is thus standard at the global level (i.e. over the experimental block) and deviant at the local level (i.e. within a single trial). The local standard sequence becomes a global deviant and triggers the occurrence of a P300 component. In sum, the 'local-global' paradigm allows orthogonal manipulations of automatic versus conscious brain responses to regularity violations.

Figure 4:
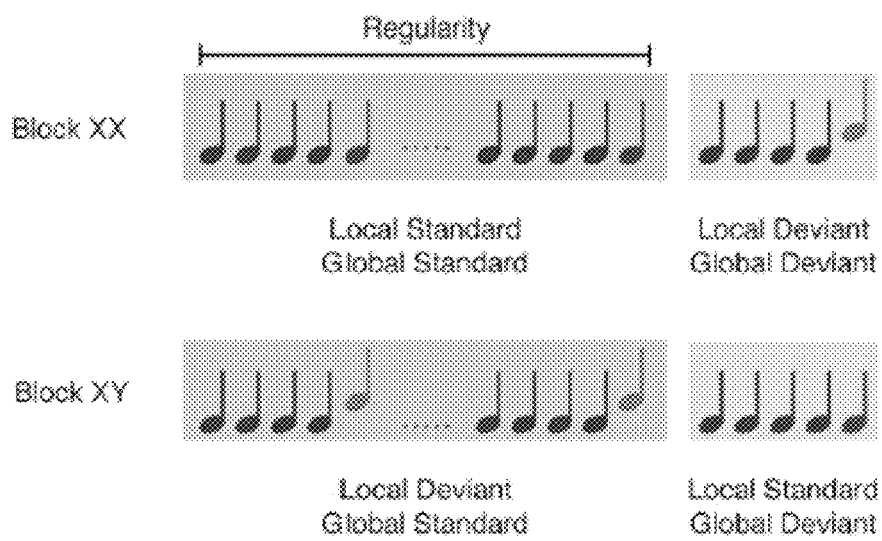
FIG. 4 is an illustration of the local global auditory paradigm according to one embodiment of the present invention.

According to the embodiment shown in FIG. 4, each auditory trial is formed by 5 consecutive sounds lasting for a predefined window ranging from a few milliseconds to hundreds of milliseconds, with a predefined gap between the auditory stimulus' onsets ranging from a few milliseconds to hundreds of milliseconds and an intertrial interval ranging from 1 to 2 milliseconds. The fifth auditory stimulus can be either equal to the first 4 (i.e. XXXXX) or different from the first 4 (i.e. XXXXY); which defines whether the trial is standard or deviant at a local (or within trial) level. The second level of regularities is defined across trials (or at a global level); frequent trials define the regularity, and rare ones violate this regularity. Frequent trial represents a percentage of the trials superior to 50% and rare trial represents remaining trials. Two types of stimulation blocks are played in the auditory stimulation: the XX blocks and XY blocks. In the XX blocks, the frequent stimulus corresponds to 5 equal auditory stimuli (local standard and global standard). In contrast, the infrequent stimulus corresponds to 4 equal auditory stimuli followed by a fifth different auditory stimulus (local deviant and global deviant). In the XY blocks, the frequent stimulus corresponds to 4 equal auditory stimuli and a fifth different auditory stimuli (local deviant and global standard), while the infrequent stimulus corresponds to 5 equal auditory stimuli (local standard and global deviant). The local effect is quantified by contrasting all local deviant trials versus all local standard trials. The global effect is quantified by contrasting all global deviant trials versus all global standard trials.

The auditory stimulation 100 is followed by the step 200 of receiving an electrocardiographic signal of the subject obtained from a recording during the generation of the auditory stimulation.

Figure 2:
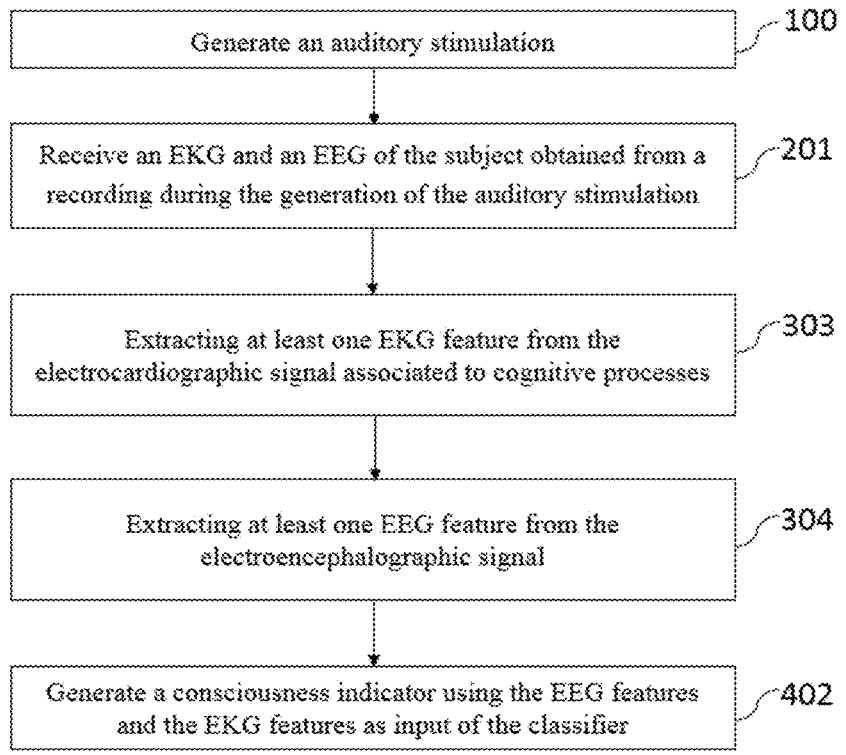
FIG. 2 is a flowchart showing the steps implemented by the method according to a second embodiment of the invention concerning the classification of subjects with disorders of consciousness using EKG features and EEG features.

According to the embodiment shown in FIG. 2, the method comprises a step 201 of receiving an electroencephalographic signal of the subject recorded during the generation of the auditory stimulation. Electroencephalographic signal may be retrieved from a medical database comprising electroencephalographic signals registered during auditory stimulation of the subjects.

In one embodiment, the electroencephalographic signal of the subject is directly measured during the generation of the auditory stimulation.

According to one embodiment, the electrocardiographic signal is extracted from the electroencephalographic signal, notably using independent component analysis.

In the embodiment of FIG. 2, the extraction step is configured to extract at least one EKG feature from the electrocardiographic signal associated to cognitive processes (303) to be used as input of a classifier to generate the consciousness indicator. In this embodiment, the extraction step further comprises the extraction of at least one EEG feature from the electroencephalographic signal so as to be a further input of the classifier for the generation of the consciousness indicator 304.

According to one embodiment, the deduction step 402 consists in providing the EKG features and/or the EEG features as input of the classifier configured to generate the consciousness indicator.

According to one embodiment, the classifier is a Support Vector Machine. In machine learning, support vector machines (SVMs) are discriminative classifiers formally defined by a separating hyperplane. The Support Vector machine of the present method may be configured to perform linear classification or non-linear classification using the pattern analysis. Indeed, in order to analyze the relevance and independence of the markers regarding the diagnosis of subjects with disorders of consciousness, multivariate pattern analysis (MVPA) could be used in combination with wrappers algorithms for the selection of pertinent markers as features for the classifier. The multivariate pattern analysis method consists in training classifiers with different sets of features and comparing the obtained performance. Based on the performance comparisons, a set of features can be defined as (1) strongly or weakly relevant, when they are partially independent and contribute to an optimal classification; or (2) irrelevant, when they do not contribute to the classification. In one example, the multivariate pattern analysis method is done using 120 EEG-extracted markers (corresponding to quantification of power spectrum and complexity in individual EEG sensors and information sharing between EEG sensors) and 8 EKG-extracted markers. In one example, the kernel function of the Support Vector Machine selected to suit the problem of the present invention is a sigmoid kernel. This Support Vector Classifier (i.e. Support Vector Machine for classification) is trained upfront to distinguish between two main classes of patient with disorders of consciousness: vegetative state/unresponsive wakefulness syndrome (VS/UWS) and minimally conscious state (MCS). A penalization parameter equal to 1 may be used.

Support vector machines (SVMs) provide the best prediction performance mainly because SVMs are designed to maximize the margin to separate two classes so that the trained model generalizes well on unseen data. Most other computer programs implement a classifier through the minimization of error occurred in training, which leads to poorer generalization.

According to one embodiment, prior to the training of the classifier, relevant EKG features and/or EEG features are automatically selected keeping the highest 20% of the ANOVA F scores. For the supervised training of the Support Vector Classifier the labelled EEG data based on the Coma Recovery Scale-Revised scores (a behavioral scale for the diagnosis of disorders of consciousness) may be used.

According to one embodiment, the EKG features obtained from the electrocardiographic signal are chosen among the following:
  heart rate,
  heart rate variability in the high frequencies,
  heart rate variability in the low frequencies,
  heart rate variability in the very low frequencies,
  cardiac modulations to the stimulation paradigm in the time interval between the onset of the $N^{th}$ stimulus and the following R peak for a local effect, and
  cardiac modulations to the stimulation paradigm in the time interval between the onset of the $N^{th}$ stimulus and the following R peak for a global effect.

According to one embodiment, at least one of the following measures is performed on the electroencephalographic signal: permutation entropy, Kolmogorov Complexity, Weighted Symmetrical Mutual Information, Alpha PSD, Normalized Alpha PSD, Beta PSD, Normalized Beta PSD, Delta PSD, Normalized Delta PSD, Theta PSD, Normalized Theta PSD, Median Power Frequency, Spectral Entropy 90, Spectral Entropy 95, Spectral Entropy, Contingent Negative Variation, short-latency auditory Potential to the first sound, mid-latency auditory Potential to the first sound, GD-GS full contrast (represent the 'Global Effect' and it corresponds to the contrast of all the Global deviant trials versus all the Global standard trials), LD-LS full contrast ('Local Effect' using all blocks and it corresponds to the contrast of all the Local deviant trials versus all the Local standard trials), LSGD-LDGS full contrast (contrast of the rare trials versus the frequent trials), LSGS-LDGD full contrast (contrast of the frequent trials versus the rare trials), Contrasted P3a (Local Deviant vs Local Standard), Contrasted P3b (Global Deviant vs Global Standard), Contrasted MMN (Local Deviant vs Local Standard), Decoding of Local Deviant vs Local Standard and Decoding of Global Deviant vs Global Standard.

According to this embodiment, the EEG features are calculated as:
  mean across epochs (times) and mean across sensors (EEG electrodes) of one of the above cited measure;
  mean across epochs and standard deviation across sensors of one of the above cited measure;
  standard deviation across epochs and mean across sensors of one of the above cited measure; and/or
  standard deviation across epochs and standard deviation across sensors of one of the above cited measure.

Support Vector Machine is one of the most popular techniques of machine learning. Other techniques such as random forest may be implemented in the method of the present invention.

Figure 3:
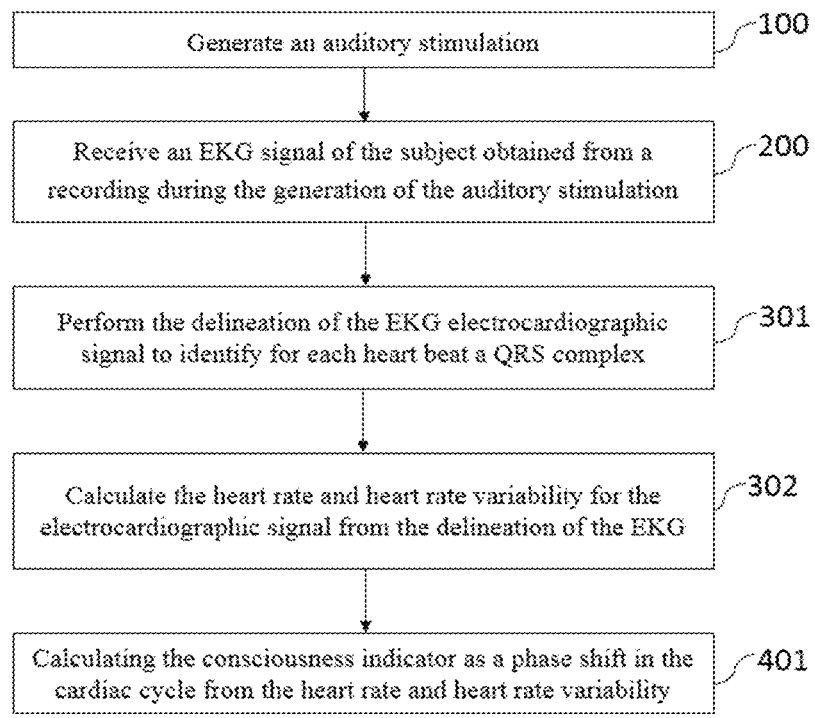
FIG. 3 is a flowchart showing the steps implemented by the method according to a first embodiment of the invention concerning the calculation of the shift in the cardiac cycle of a subject under auditory stimulation.

According to the embodiment represented in FIG. 3, the extraction step 300 and the deduction step 400 comprise:
  a) performing a delineation of the EKG electrocardiographic signal identifying for each heart beat a QRS complex (301);
  b) calculating the heart rate and heart rate variability for the electrocardiographic signal from the delineation of the EKG electrocardiographic signal (302);
  c) defining for each auditory trial a time interval as the interval between the onset of the $N^{th}$ auditory stimulus and the following R peak and calculating the consciousness indicator as a phase shift in the cardiac cycle in the time interval (401).

The delineation step 301 of this embodiment may be performed with algorithm based on wavelet transform or classification method such as Support Vector machine, or a combination thereof.

Figure 5:
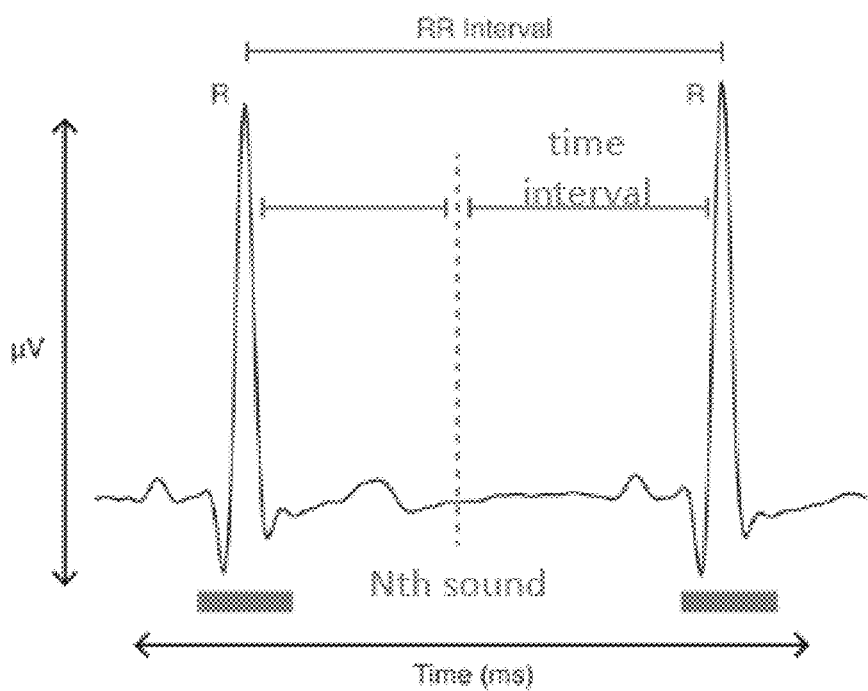
FIG. 5 is an illustration of a RR interval in an EKG signal and time interval between the onset of the $N^{th}$ auditory stimulus and the following R peak.

FIG. 5 shows two consecutives electrocardiographic QRS complexes defining an RR interval. This image shows as well the time interval between the onset of the $N^{th}$ auditory stimulus and the following R peak.

According to one embodiment, R peak onsets were obtained automatically by the algorithm described in Elgendi (Elgendi M., "*Fast QRS detection with an optimized knowledgebased method: evaluation on* 11 *standard ECG databases.*" PLoS One 2013; 8:e73557).

According to one embodiment, the step 302 comprises the calculation of the heart rate computed by averaging the differences between consecutive R peaks during the whole recording.

According to one embodiment, calculating heart rate variability for the electrocardiographic signal comprises the estimation of heart rate variability spectral variables. Such heart rate variability spectral variables which are obtained by computing the power spectrum decomposition on the point events time series from the detected R peaks. Power spectral density may be estimated in whole recording using Welch's method. In one example, the power spectral density is estimated in whole recording using Welch's method with 32.768 samples (131.072 seconds) per segment and 28.672 samples (114.688 seconds) overlap using a Hanning window. Heart rate variability variables are extracted from the sum of the spectral power in 3 frequency bands: very low frequency (i.e. range 50-0.04 Hz), low frequency (i.e. range 50.04-0.15 Hz) and high frequency (i.e. range 50.15-0.4 Hz).

According to one embodiment, the consciousness indicator is compared to a threshold.

The present invention further relates to a system 1 for the generation of a consciousness indicator for a non-communicating subject. The main components of the system are a stimuli generator 2, an extraction module 3 and a calculation module 4.

According to one embodiment, the stimuli generator 2 is configured to generate an auditory stimulation according to the embodiment described here above.

According to one embodiment, the system 1 comprises an acquisition module configured to perform the acquisition of an electroencephalographic signal during the auditory stimulation of the patient. The system may be configured to control a high density electroencephalogram positioned onto the scalp of the subject. The communication with the high density electroencephalogram to control acquisition and retrieve data may be performed through a communication module, notably equipped to perform wireless data transfer.

According to one embodiment, the extraction module 3 is configured to obtain an electrocardiographic signal of the subject during the generation of the auditory stimulation. In one embodiment, the extraction module 3 receives electroencephalographic signal of the subject acquired during the generation of the auditory stimulation. In this embodiment, the electrocardiographic signal is extracted from the electroencephalographic signal according to the embodiments describe hereabove.

According to one embodiment, the calculation module 4 is configured to extract at least one feature from the electrocardiographic signal and deduce a consciousness indicator from an analysis of the electrocardiographic features according to the embodiment described hereabove.

The steps of the method implemented by the different modules described herein are implemented by hardware components. Examples of hardware components include controllers, sensors, generators, drivers, memories, comparators, arithmetic logic units, adders, subtractors, multipliers, dividers, integrators, neural networks, signal separators, calculators, extractors, determiners, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the steps described herein. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The present invention further relates to a program comprising instructions which, when the program is executed by a computer, cause the computer to carry out the steps of the method according to any one of the embodiments described here above.

Instructions of the program, to perform the methods as described above, are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

Yet another aspect of the present invention relates to a computer-readable storage medium comprising instructions which, when the program is executed by a computer, cause the computer to carry out the steps of the computer-implemented method according to anyone of the embodiments described here above. According to one embodiment, the computer-readable storage medium is a non-transitory computer-readable storage medium.

Computer programs implementing the method of the present embodiments can commonly be distributed to users on a distribution computer-readable storage medium such as, but not limited to, an SD card, an external storage device, a microchip, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While various embodiments have been described and illustrated, the detailed description is not to be construed as being limited hereto. Various modifications can be made to the embodiments by those skilled in the art without departing from the true spirit and scope of the disclosure as defined by the claims.

Examples

The present invention is further illustrated by the following example.

Example:
Subjects and Methods
Subjects

Subjects admitted for consciousness evaluation at Neurological Departments were included. The neurological evaluation of the patients' disorders of consciousness was performed by trained clinicians, including the Coma Recovery Scale-Revised (CRS-R). CRS-R scoring ranges from 0 to 23 and is based on the presence or absence of response on a set of hierarchically ordered items testing auditory, visual, motor, oromotor, communication, and arousal functions. Behavioral evaluations were performed systematically before each EEG recording.

Only EEG recordings were used and EKG time series were obtained using independent component analysis (ICA) on the EEG recordings for each patient. The current analysis only used the temporal location of the R wave peaks.

Subjects having unclear EEG recording or EKG reconstructed source that produced at least 40 samples for each stimulation block type were rejected. There were no differences between the included and excluded patients in terms of diagnostic state and sex. Included patients were older than excluded patients and more patients suffered from anoxic as compared to traumatic injuries in the included group compared to the excluded group.

A final cohort of 127 patients remained: 70 in vegetative state/unresponsive wakefulness syndrome (VS/UWS) and 57 in minimally conscious state (MCS). Subject groups did not differ in terms of gender, etiologies, and chronicity. MCS subjects were older than VS/UWS subjects. No subject had any history of cervical spinal cord injury or symptoms of autonomic dysfunction (eg, hemodynamic instability, abnormal HRV) at the time of EEG recording.

Auditory Stimulation and EEG

Cognitive processing was prompted by means of the EEG based auditory local-global paradigm. Each auditory trial was formed by 5 consecutive sounds lasting 50 milliseconds, with a 150-millisecond gap between the auditory stimulus' onsets and an intertrial interval ranging from 1.350 to 1.650 milliseconds. The frequent trial represented the 80% of the trials and the rare trial represent the 20% of all trials.

Subject were stimulated vocally between each stimulation block and with tactile stimulations if subject appeared asleep. A mask may be applied on the eyes to normalize the eyes open/closed.

EEG recordings were performed using a NetAmps 300 amplifier (Electrical Geodesics, Eugene, Oreg.) at a sampling rate of 250 Hz with a 256-electrode HydroCel Geodesic Sensor Net (Electrical Geodesics) referenced to the vertex.

EKG Extraction from EEG

EKG was extracted from the EEG using independent component analysis (ICA). The independent components (ICs) corresponding to the electrocardiographic signal were selected by visual inspection based on the spatial and temporal representation of the QRS complex. The raw electroencephalographic data were first filtered using an eight-order low-pass Butterworth filter at 45 Hz and a fourth order high-pass filter at 0.5 Hz. Secondly, three different ICA decompositions were computed:

FastICA, parametrized to obtain the components that explain 99% of the variance and computed from raw filtered data;

INFOMAX, parametrized to obtain 256 components from raw filtered data; and

INFOMAX in combination to artifact channels rejection.

Individual channels were removed when the temporal variance was superior to 3 standard deviations away from the mean of the variance of the rest of the channels. The independent components with the electrocardiographic information were selected based on the time series and the weights' topographies by visual inspection. The selected time series had to clearly contain the R peak corresponding to the QRS complex. The R peak had to be easily detected by using a simple threshold. The corresponding topography had to concentrate the mixing weights on the frontal right and posterior left electrodes. These electrodes were located in the right cheek, left maxillary junction, and underneath the left mastoid, as depicted by previous studies on cardiac electrical fields. The algorithm that presented the clearest decomposition, usually the one with the highest rank in descending order of explained variance, was selected. Finally, R peak onsets were obtained automatically by the algorithm described in Elgendi. Subjects for whom the EKG component was unclear were excluded from the analysis. Exclusion criteria were set to any of the following: EKG reconstructed signal with no clear R peaks, detection failure by the automatic algorithm, or topography of corresponding weights with a mix of peripheral and central electrodes.

Cardiac Cycle Modulation Induced by the Auditory Stimulation Protocol

To evaluate potential phase shifts in the cardiac cycle associated with the processing of different types of auditory stimuli, 2 intervals temporally locked to the onset of the fifth sound were defined the PRE interval, that is, the interval between the heartbeat (defined by the location of the R peak) preceding the stimulus and the onset of the auditory stimulation; and (2) the POST interval, that is, the interval between the stimulus onset and the following heartbeat. All time intervals were then labeled according to the contained auditory stimulation following the local-global paradigm (XX block: LSGS or LDGD; XY block: LDGS or LSGD). Finally, in order to avoid using peaks without a clearly defined temporal association to a given heartbeat (and not the previous or following one), the analysis was restricted to the trials in which both the PRE and POST intervals were between 20 and 600 milliseconds. A repeated measures Bayesian analysis of variance (ANOVA) was computed for each interval using the ratio of rejected trials as the study variable and the trial label and clinical state as factors. The PRE and POST stimulus intervals were analyzed for each group of subjects in relation to the type of trials. For the local effect, each subject mean of the PRE and POST intervals corresponding to LD trials was subtracted from the mean of the LS ones. Similarly, for the global effect, the mean of the PRE and POST intervals corresponding to GD trials was subtracted from the mean of GS ones.

Multivariate Patient Classification by Means of EKG and EEG Markers

To analyze the relevance and independence of the markers regarding the diagnosis of DOC, it was used multivariate pattern analysis (MVPA) in combination with wrappers algorithms for feature selection. MVPAs were done using 120 EEG-extracted markers (corresponding to quantification of power spectrum and complexity in individual EEG sensors and information sharing between EEG sensors) and 8 EKG-extracted markers. and 8 EKG-extracted markers. The support vector classifier (SVC) was trained to distinguish between the VS/UWS and the MCS patients with a penalization parameter equal to 1. The SVC was repeatedly cross-validated with randomized stratified k-folding (k58). Previously to the training of the classifier, relevant features were automatically selected keeping the highest 20% of the ANOVA F scores. Performance of the classifier was measured using area under the curve (AUC) scores. We defined 3 sets of features: (1) EKG markers of cognitive processes, corresponding to the PRE and POST intervals for the local and global contrasts (termed EKGcog); (2) EKG markers of baseline vegetative function (termed EKGveg), corresponding to the HR and HRV at the 3 frequencies previously defined; and (3) EEG markers. We estimated the accuracy of the classification algorithm with 6 different combinations of these sets of markers: (1) EEG+EKGcog+EKGveg, (2) EEG+EKGcog, (3) EEG+EKGveg, (4) EEG markers only, (5) EEG with both EKGcog and EKGveg markers shuffled, and (6) EKGcog+EKGveg markers only. To minimize the effect of the random selection of folds, the AUC scores were averaged across 250 repetitions.

Results

Cardiac Cycle Modulation Induced by the Auditory Stimulation Protocol

Figure 6:
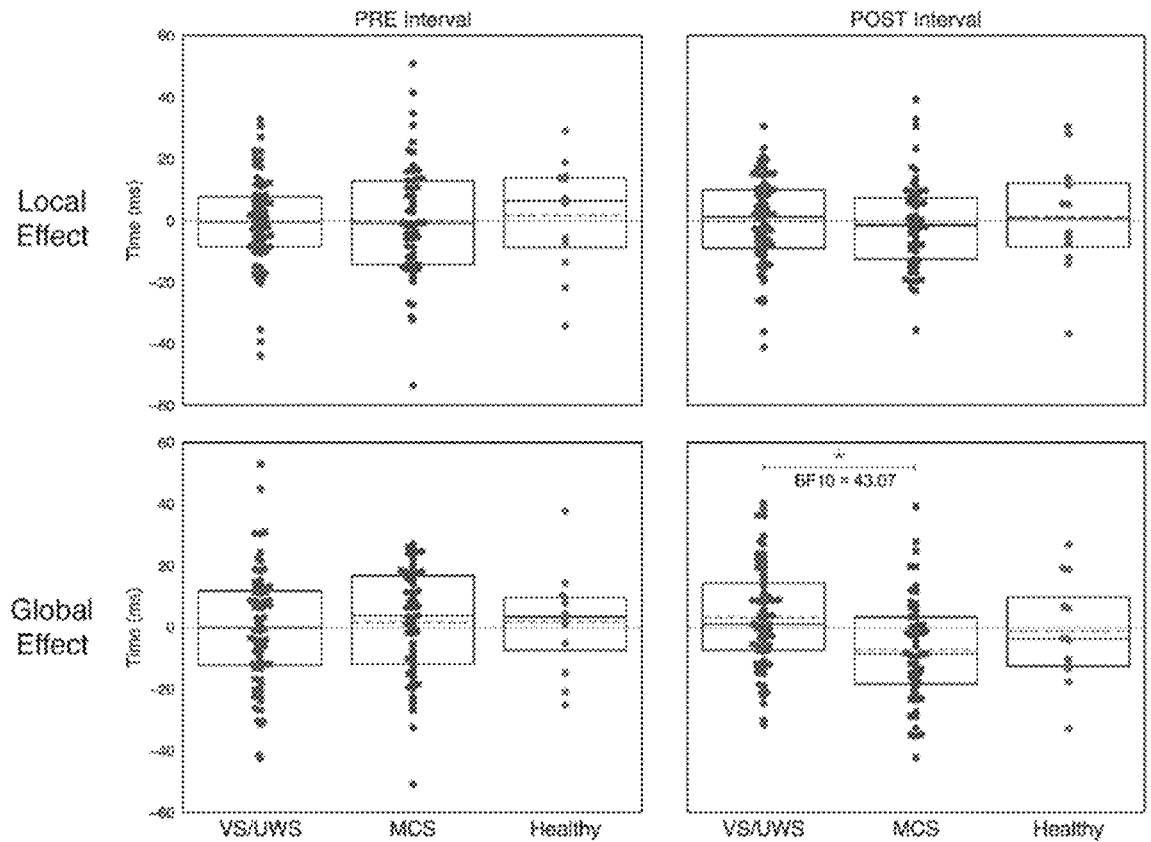
FIG. 6 comprises multiple boxplots presenting some experimental results concerning the evaluation of the shift in the cardiac phase. Boxplots with interquartile range, median (solid line), and mean (dashed line) represent the distribution of data in the clinical groups.

FIG. 6 shows that violations of global regularities induce cardiac cycle phase acceleration only in minimally conscious patients. Each dot represents a patient in vegetative state/unresponsive wakefulness syndrome (VS/UWS, n=70) or in minimally consciousness state (MCS, n=57), or a healthy control (Healthy, n=12). Boxplots with interquartile range, median (black line), and mean (dashed line) represent the distribution of data in the clinical groups. There was no evidence for difference in cardiac cycle modulation between groups due to the processing of the local regularities in either the PRE or the POST intervals (FIG. 6). Within the groups, neither the VS/UWS nor the MCS patients presented significant differences between LS and LD trials. In the case of the global effect, there was no evidence of modulation difference between groups due to the global auditory processing in the PRE interval. On the contrary, in the POST interval, there was strong evidence for a difference between the MCS and VS/UWS groups.

Multivariate Patient Classification by Means of EKG and EEG Markers

Figure 7:
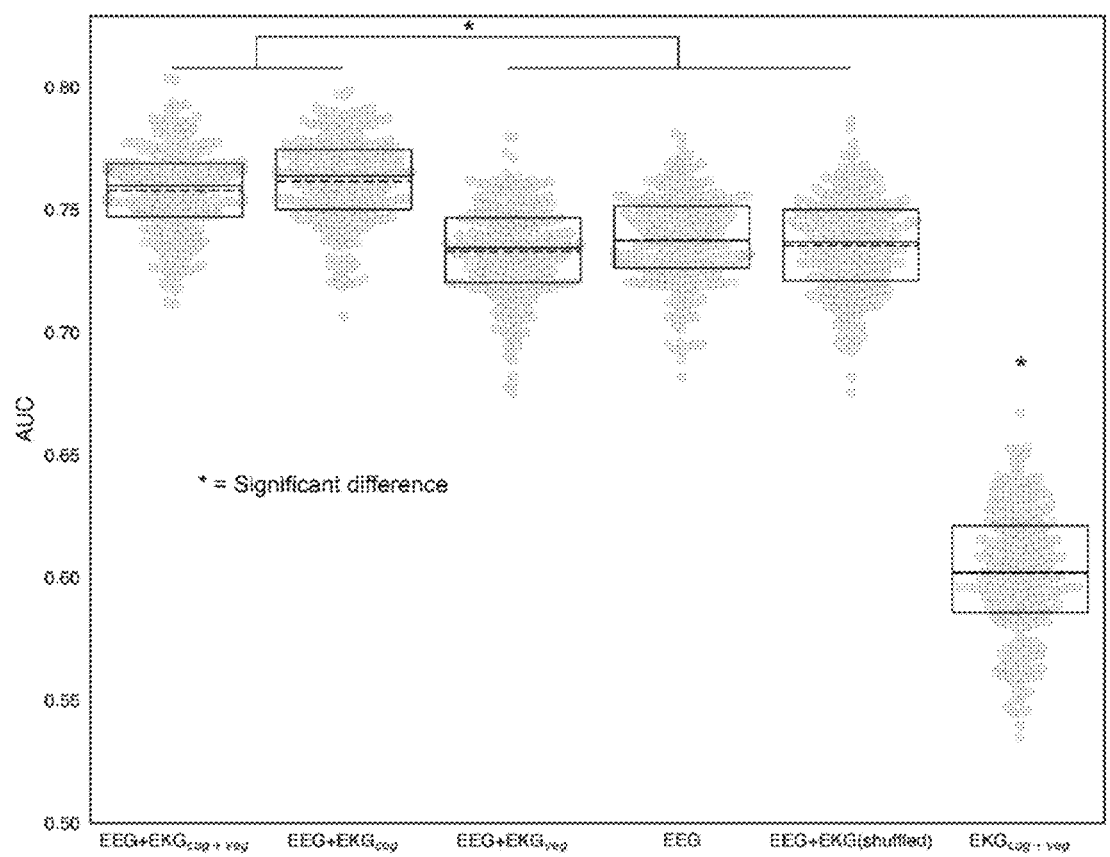
FIG. 7 comprises a boxplot presenting some experimental results concerning the evaluation subject's consciousness using classification. Boxplots with interquartile range, median (solid line), and mean (dotted line) represent the distribution of values for each set of features.

Six distinct multivariate classifiers were trained to distinguish between vegetative state/unresponsive wakefulness syndrome and minimally conscious state patients using different combinations of EKG and EEG markers. Multivariate analysis combining EEG and EKGcog showed better performance compared to EEG and EKGveg markers and EEG markers alone (FIG. 7). Combining the EKGcog and EEG markers led to an improvement of the performance (EEG+EKGcog, AUC=76.1; EEG+EKGcog+EKGveg, AUC=75.7). Conversely, when EKGcog markers were not included in the MVPA, the performance did not differ from EEG alone (EEG only, AUC=73.7; EEG+EKGveg, AUC=73.3). As a control test for the effect of the number of features, classification was also computed combining EEG and label-shuffled EKG markers; in this case, the AUC was estimated at 73.6. Using solely cardiac markers, the classifier performed above chance, with a mean AUC of 60.1. Comparing the performance of MVPAs that included EEG features, it was only found significant differences when the MVPAs also included EKGcog versus when the MVPAs did not include these cardiac features. The inclusion of EKGveg features did not significantly change the performance of the tested MVPA classifiers. Therefore, this analysis shows that cognitive electrocardiographic markers carry partially independent information from electroencephalography.

The invention claimed is:

1. A computer-implemented method for the generation of a consciousness indicator for a non-communicating subject to be used in the evaluation of a state of consciousness of said non-communicating subject, comprising:

generating an auditory stimulation, said auditory stimulation comprising multiple auditory trials having a predefined intertrial interval, each auditory trial formed by N consecutive auditory stimuli having a predefined time duration with a predefined gap between the auditory stimuli onsets, wherein the auditory stimulation comprises a first percentage of local standard trials comprising N identical auditory stimuli and a second percentage of locally deviant trials comprising the first N-1 identical auditory stimuli and the $N^{th}$ auditory stimulus different from the preceding N-1 auditory stimuli, wherein N is equal or superior to 2, said auditory stimulation being adapted to be heard by the non-communicating subject so as to prompt cognitive processes in the non-communicating subject;

receiving an electrocardiographic signal and an electroencephalographic signal of the subject obtained during the generation of the auditory stimulation;

extracting from the electrocardiographic signal at least one electrocardiographic EKG feature representative of the occurrence of cognitive processes, wherein at least one of said at least one electrocardiographic EKG feature is selected among the following:

■ a time interval between the onset of the $N^{th}$ stimulus of one local standard trial and a following R peak;
■ a time interval between the onset of the $N^{th}$ stimulus of one locally deviant trial and the following R peak;
■ a time interval between an R peak preceding the $N^{th}$ stimulus of one local standard trial and the onset of said $N^{th}$ stimulus of one local standard trial;
■ a time interval between the R peak preceding the $N^{th}$ stimulus of one locally deviant trial and the onset of the $N^{th}$ stimulus of said one locally deviant trial;

extracting from the electroencephalographic signal at least one electroencephalographic EEG feature representative of the occurrence of cognitive processes;

using the at least one EEG feature and said at least one EKG feature as input to a classifier to generate said consciousness indicator, said classifier having been previously trained using a machine learning technique.

2. The method according to claim 1, wherein the received electrocardiographic signal is extracted from the electroencephalographic signal.

3. The method according to claim 1, further comprising a step of comparison of the consciousness indicator to a predefined threshold.

4. The method according to claim 1, further comprising extracting at least one EKG vegetative feature representative of baseline vegetative function of the subject from the electrocardiographic signal, and using said at least one EKG vegetative feature as additional input to the classifier, in addition to the at least one EEG feature and said at least one EKG feature.

5. A non-transitory computer readable medium comprising instructions which when executed by a computer, cause the computer to carry out the following steps:

generating an auditory stimulation, said auditory stimulation comprising multiple auditory trials having a predefined intertrial interval, each auditory trial formed by N consecutive auditory stimuli having a predefined time duration with a predefined gap between the auditory stimuli onsets, wherein the auditory stimulation comprises a first percentage of local standard trials comprising N identical auditory stimuli and a second percentage of locally deviant trials comprising the first N-1 identical auditory stimuli and the $N^{th}$ auditory stimulus different from the preceding N-1 auditory stimuli, wherein N is equal or superior to 2, said auditory stimulation being adapted to be heard by a non-communicating subject so as to prompt cognitive processes in the non-communicating subject;

receiving an electrocardiographic signal and an electroencephalographic signal of the subject obtained during the generation of the auditory stimulation;

extracting at least one electrocardiographic EKG feature from the electrocardiographic signal representative of the occurrence of cognitive processes; wherein at least one of said at least one electrocardiographic EKG feature is selected among the following:
- ■ a time interval between the onset of the $N^{th}$ stimulus of one local standard trial and a following R peak;
- ■ a time interval between the onset of the $N^{th}$ stimulus of one locally deviant trial and the following R peak;
- ■ a time interval between an R peak preceding the $N^{th}$ stimulus of one local standard trial and the onset of said $N^{th}$ stimulus of one local standard trial;
- ■ a time interval between the R peak preceding the $N^{th}$ stimulus of one locally deviant trial and the onset of the $N^{th}$ stimulus of said one locally deviant trial;

extracting from the electroencephalographic signal at least one electroencephalographic EEG feature representative of the occurrence of cognitive processes;

using the at least one EEG feature and said at least one EKG feature as input to a classifier to generate said consciousness indicator, said classifier having been previously trained using a machine learning technique.

6. A system for the generation of a consciousness indicator for a non-communicating subject, comprising at least one processor configured to:

generate an auditory stimulation, said auditory stimulation comprising multiple stimulation trials having a predefined intertrial interval, each stimulation trial formed by N consecutive auditory stimuli having a predefined time duration with a predefined gap between the auditory stimuli onsets, wherein the auditory stimulation comprises a first percentage of local standard trials comprising N identical auditory stimuli and a second percentage of locally deviant trials comprising the first N-1 identical auditory stimuli and the $N^{th}$ auditory stimulus different from the preceding N-1 auditory stimuli, said auditory stimulation being adapted to be heard by the non-communicating subject so as to prompt cognitive processes in the non-communicating subject;

obtain an electrocardiographic signal and an electroencephalographic signal of the subject during the generation of the auditory stimulation; and extract at least one electrocardiographic EKG feature from the electrocardiographic signal representative of the occurrence of cognitive processes; wherein at least one of said at least one electrocardiographic EKG feature is selected among the following:
- ■ a time interval between the onset of the $N^{th}$ stimulus of one local standard trial and a following R peak;
- ■ a time interval between the onset of the $N^{th}$ stimulus of one locally deviant trial and the following R peak;
- ■ a time interval between an R peak preceding the $N^{th}$ stimulus of one local standard trial and the onset of said $N^{th}$ stimulus of one local standard trial;
- ■ a time interval between the R peak preceding the $N^{th}$ stimulus of one locally deviant trial and the onset of the $N^{th}$ stimulus of said one locally deviant trial;

extracting from the electroencephalographic signal at least one electroencephalographic EEG feature representative of the occurrence of cognitive processes;

using the at least one EEG feature and said at least one EKG feature as input to a classifier to generate said consciousness indicator, said classifier having been previously trained using a machine learning technique.

7. The system according to claim 6, wherein the received electrocardiographic signal is extracted from the electroencephalographic signal.

8. The system according to claim 6, wherein the at least one processor is further configured to compare the consciousness indicator to a predefined threshold.

9. The system according to claim 6, wherein the classifier is a support vector machine previously trained to distinguish between two classes: vegetative state/unresponsive wakefulness syndrome (VS/UWS) and minimally conscious state (MCS).

* * * * *